(12) United States Patent
Beckstead et al.

(10) Patent No.: US 8,687,177 B2
(45) Date of Patent: Apr. 1, 2014

(54) SYSTEM AND METHOD FOR COMBINED RAMAN AND LIBS DETECTION

(75) Inventors: Jeff Beckstead, Valencia, PA (US); Matthew Nelson, Harrison City, PA (US); Patrick Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 696 days.

(21) Appl. No.: 12/899,055

(22) Filed: Oct. 6, 2010

(65) Prior Publication Data

US 2011/0085165 A1    Apr. 14, 2011

Related U.S. Application Data

(63) Continuation-in-part of application No. 11/656,393, filed on Jan. 23, 2007, now Pat. No. 7,999,928.

(60) Provisional application No. 61/278,393, filed on Oct. 6, 2009.

(51) Int. Cl.
*G01N 21/00* (2006.01)

(52) U.S. Cl.
USPC ............. 356/73.1; 356/73; 356/301; 356/446

(58) Field of Classification Search
USPC ................... 356/73, 73.1, 445, 446, 301, 451
See application file for complete search history.

(56) References Cited

U.S. PATENT DOCUMENTS

| | | |
|---|---|---|
| 4,880,052 A | 11/1989 | Meyer |
| 5,194,912 A | 3/1993 | Batchelder |
| 5,377,004 A | 12/1994 | Owen |
| 5,442,438 A | 8/1995 | Batchelder |
| 5,528,393 A | 6/1996 | Sharp |
| 5,539,517 A | 7/1996 | Cabib |
| 5,623,342 A | 4/1997 | Baldwin |
| 5,689,333 A | 11/1997 | Batchelder |
| 5,710,626 A | 1/1998 | O'Rourke |
| 5,862,273 A | 1/1999 | Pelletier |
| 5,866,430 A | 2/1999 | Grow |

(Continued)

FOREIGN PATENT DOCUMENTS

JP    9121889    5/1997

OTHER PUBLICATIONS

Caetano et al, "Evaluation of the Importance of Non-Linear Spectral Mixing in Coniferous Forests," SPIE vol. 3499, Sep. 1998, pp, 257-269.

(Continued)

*Primary Examiner* — Gregory J Toatley
*Assistant Examiner* — Iyabo S Alli

(57) ABSTRACT

A system and method for detection and identification of unknown samples using a combination of Raman and LIBS detection techniques. A first region of a sample and a second region of a sample are illuminated using structured illumination to thereby generate a first plurality of interacted photons and a second plurality of interacted photons. This first plurality and second plurality of interacted photons may be passed through a fiber array spectral translator device. Said first plurality of interacted photons are assessed using Raman spectroscopy to thereby generate a Raman data set. Said second plurality of interacted photons are assessed using LIBS spectroscopy to thereby generate LIBS data set. These data sets may be analyzed to identify the sample. These data sets may also be fused for further analysis.

31 Claims, 12 Drawing Sheets

(56) References Cited

U.S. PATENT DOCUMENTS

| | | | |
|---|---|---|---|
| 5,901,261 | A | 5/1999 | Wach |
| 5,911,017 | A | 6/1999 | Wach |
| 6,002,476 | A | 12/1999 | Treado |
| RE36,529 | E | 1/2000 | Lewis |
| 6,717,668 | B2 | 4/2004 | Treado |
| 6,954,667 | B2 | 10/2005 | Treado |
| 6,965,793 | B2 | 11/2005 | Treado |
| 6,992,809 | B1 | 1/2006 | Wang |
| 7,362,489 | B2 | 4/2008 | Wang |
| 7,474,685 | B2 | 1/2009 | Kalayeh |
| 7,542,138 | B2 | 6/2009 | Gardner |
| 7,692,775 | B2 | 4/2010 | Treado |
| 2008/0088837 | A1* | 4/2008 | Gardner, Jr. ............ 356/300 |
| 2009/0128802 | A1 | 5/2009 | Treado |

OTHER PUBLICATIONS

Rasmussen et al, "Library Retrieval of Infrared Spectra Based on Detailed Intensity Information," Applied Spectroscopy, vol. 33, No. 4, Feb. 1979, pp. 371-376.

Guilment et al, "Infrared Chemical Micro-Imaging Assisted by Interactive Self-Modeling Multivariate Analysis," Applied Spectroscopy, vol. 48, No. 3, 1994, pp. 320-326.

Malinowski, :Factor Analysis in Chemistry, 1991, 2nd Edition, Published by John Wiley and Sons, Inc. William H. Press, et al, pp. 208-265.

Marquardt, et al, "Novel Probe for Laser-Induced Breakdown Spectroscopy and Raman Measurements Using an Imaging Optical Filter," Applied Spectroscopy, 1998, p. 1148-1153, vol. 52. No. 9.

Wiens et al, "Development of a Prototype Laser-Induced Breakdown Spectroscooy (LIBS) instrument with Standoff Distances," Spectrochimica Acta Part A vol. 61, issue 10. Aug. 2005, p. 2324-2334.

Thompson et al, Combined Remote LIBS and Raman Spectroscopy Measurements, Lunar and Planetary Science Conference, XXXVI, #1517, Houston, Texas, Mar. 14-18, 2005, (available at : http://www.lpi.ursa.edu/meetings/lpsc2005/pdf/1517.pdf), last accessed Sep. 23, 2008.

Hubble et al, A Combined Remote LIBS and Raman Spectroscopy Study of Minerals, Lunar and Planetary Science Conference, XXXIII, #1935, Houston, Texas, Mar. 11-15, 2002, (Available at: http:www.lpi.usra.edu/meetings/lpsc2002/pdf/1935.pdf), last accessed Sep. 23, 2008.

Wiens, et al, "Joint Analysis by Laser-Induced Breakdown Spectroscopy (LIBS) and Raman Spectroscopy at Standoff Systems," Spectrochimica Acta Part A 61 (2005) 232-2334.

* cited by examiner

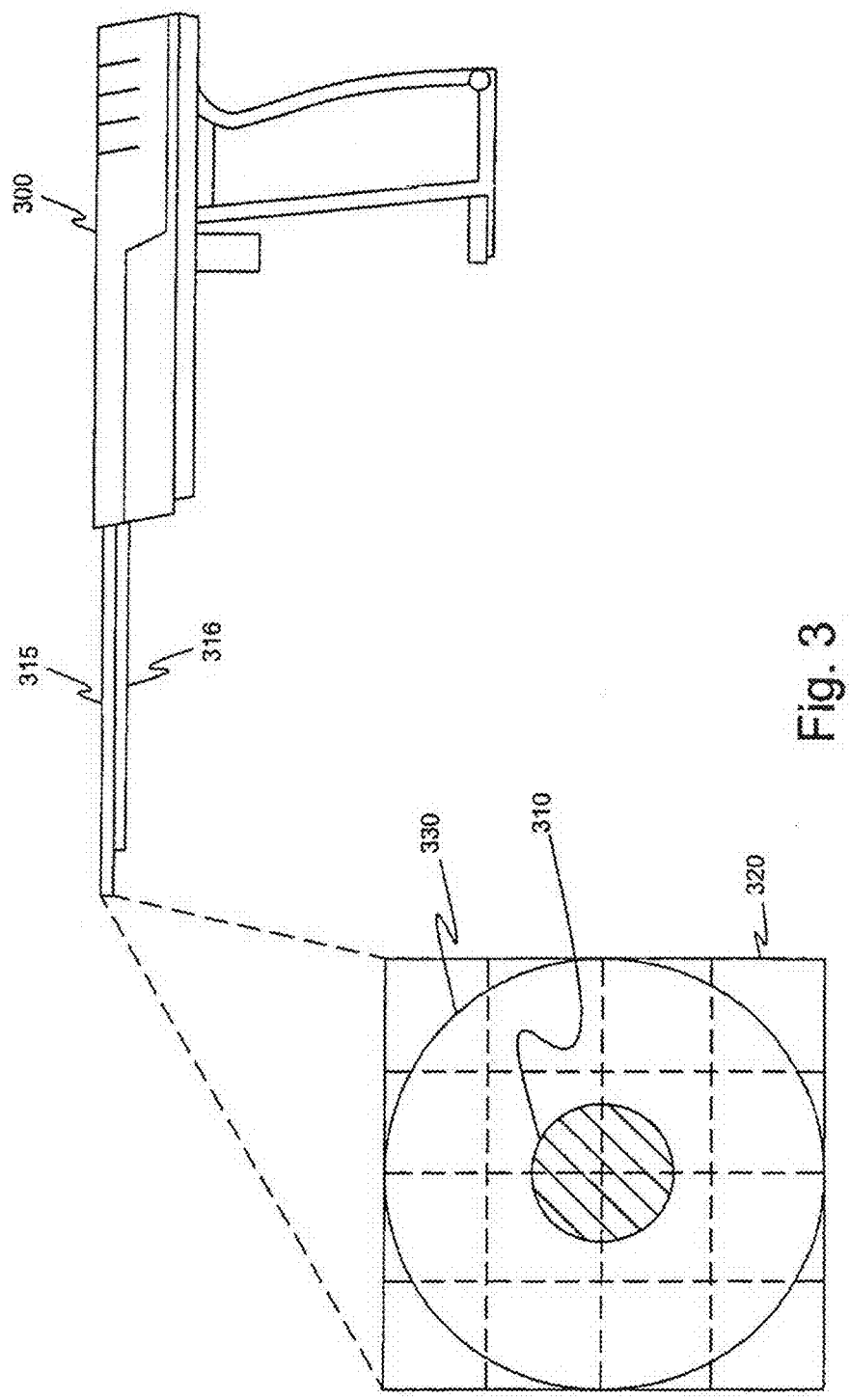

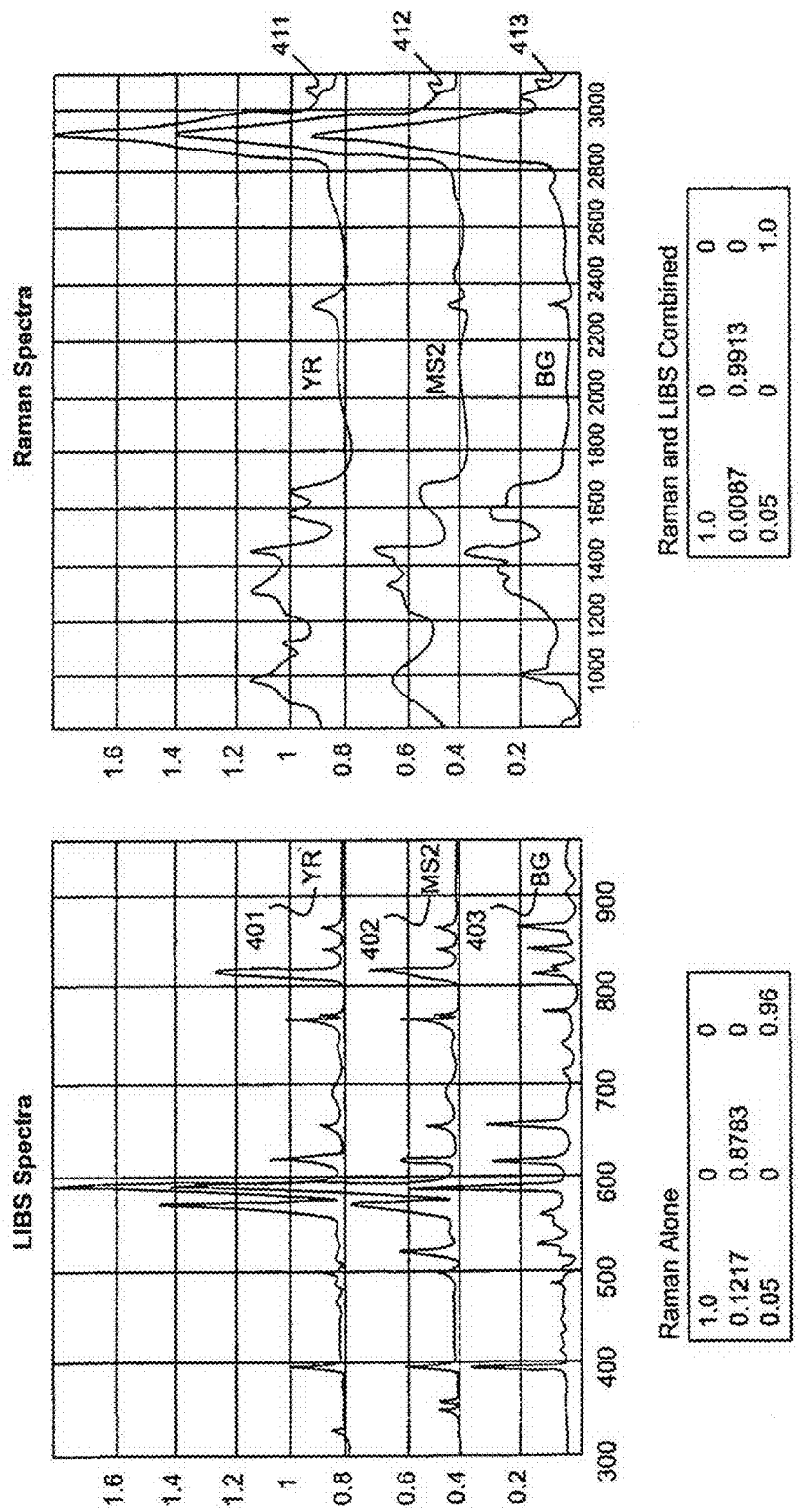

SYSTEM AND METHOD FOR COMBINED RAMAN AND LIBS DETECTION

RELATED APPLICATIONS

This application is a continuation-in-part of pending U.S. patent application Ser. No. 11/656,393, filed on Jan. 23, 2007, entitled "Method and System for Combined Raman and Libs Detection." This application also claims priority to U.S. Provisional Patent Application No. 61/278,393, filed on Oct. 6, 2009, entitled "Use of Magnification to increase SWIR HSI Detection Sensitivity." These patents and patent applications are hereby incorporated by reference in their entireties.

BACKGROUND

Deployment of threat agents poses significant threats to both human and economic health. The threat is compounded by a limited ability to detect deployment of the agents. Prior art detection strategies rely on separate instrumentation for detection and identification of the threat agent. Conventional means of detecting airborne matter include relatively non-specific optical and spectroscopic methods, including laser scattering and ultraviolet laser induced fluorescence (UV-LIF). Conventional means to identify a threat agent include wet chemical methods or spectroscopic methods. Reagent-based identification of biological threat agents includes methods such as specific antibodies, genetic markers and propagation in culture. While highly specific, these identification methods are time-consuming, labor-intensive and costly.

Spectroscopic means, for identification, provide an alternative to reagent-based identification methods and include mass spectrometry, infrared spectroscopy, Raman spectroscopy, laser induced breakdown spectroscopy (LIBS), and imaging spectrometry. Mass spectrometry is limited by sensitivity to background interference. Infrared spectroscopy exhibits low sensitivity. Raman spectroscopy is a good candidate for detection of threat agents based on its ability to provide a molecular "fingerprint" for materials with high specificity. Raman spectroscopy can be implemented in several different configurations, including normal Raman spectroscopy, UV resonance Raman spectroscopy, surface enhanced Raman spectroscopy (SERS) and non-linear Raman spectroscopy.

While normal Raman spectroscopy has demonstrated adequate sensitivity and specificity for detection of airborne matter, other forms of Raman spectroscopy suffer from inadequate sensitivity, specificity or signature robustness. LIES is also a good candidate for detection of threat agents based on its ability provide an elemental "fingerprint" for materials with high sensitivity. Prior art imaging spectroscopy is limited by the need to switch from a broadband light source, for optical imaging, to a substantially monochromatic light source for spectroscopic imaging. This results in a signification delay and inefficiency during detection during which the sample may degrade.

In order to improve the overall sensitivity and specificity of a fieldable threat detection, the invention combines two well known and proven techniques, Raman and LIBS, into a system optimized for threat detection. Both individual methods have demonstrated the ability to detect threats in point sensing, proximity sensing and standoff sensing configurations. Improved overall detection performance can be realized through appropriate chemometric spectral processing algorithms applied to the fused data of the two orthogonal techniques. By combining Raman and LIBS techniques, threat detection performance can be improved relative to the individual techniques acting alone.

SUMMARY OF THE INVENTION

The present disclosure relates to systems and method for the detection and/or identification of unknown samples using a combination of Raman and LIBS spectroscopic techniques. More specifically, the present disclosure relates to systems and methods for the detection and/or identification of explosive materials using a combination of Raman and LIBS spectroscopic techniques in conjunction with a fiber array spectral translator device and time-gated detection. The present disclosure also provides for detection of Raman and LIBS data using a single spectrometer. These improvements hold potential for reduction of system size, weight, and power consumption.

BRIEF DESCRIPTION OF THE DRAWINGS

These and other embodiments of the disclosure will be discussed in relation to the following non-limiting and exemplary drawings, in which:

FIG. 3 is a schematic representation for an apparatus according to one embodiment of the disclosure;

FIGS. 4A and 4B respectively show LIBS and Raman spectra of a sample; and

DETAILED DESCRIPTION

Raman spectroscopy has emerged as an attractive candidate for reagentless detection technology and shows significant capabilities in controlled studies for field detection of both chemical, Radiological, nuclear, and explosive (CBRNE) biological agents. Specifically, Raman sensing is being exploited for chemical surface contamination, on-the-move detection, white powder identification using handheld Raman sensors, and for waterborne pathogen detection. However, For identifying certain bio-chemical agents, Raman detection fails to provide a conclusive determination.

Laser Induced Breakdown Spectroscopy (LIBS) is a type of atomic emission spectroscopy which uses a highly energetic laser pulse as the excitation source. Because all substances emit light when excited to sufficiently high temperatures, LIBS can detect all elements, limited only by the power of the laser as well as the sensitivity and wavelength range of the spectrograph and the detector. The development of the broadband, high-resolution spectrometer, along with advanced chemometric approaches, has enabled LIBS to demonstrate real-time detection and discrimination of hazardous chemical, biological and explosive (CBRNE) materials. Operationally, LIBS is very similar to are/spark emission spectroscopy. The laser pulses delivered to the sample can be mildly destructive of the sample. However, the laser pulses can be directed to a specific region of the sample, making the surrounding sample material available for Raman sampling.

Thus, according to one embodiment of the disclosure an integrated detection system synergistically combines Raman detection mode with LIBS technologies to provide an integrated and efficient detection system. The combined Raman/LIBS sensory system can provide reagentless sensing technology for the detection and identification of chemical or biological agents. In another embodiment, the disclosure relates to a structured method and apparatus.

Figure 1:
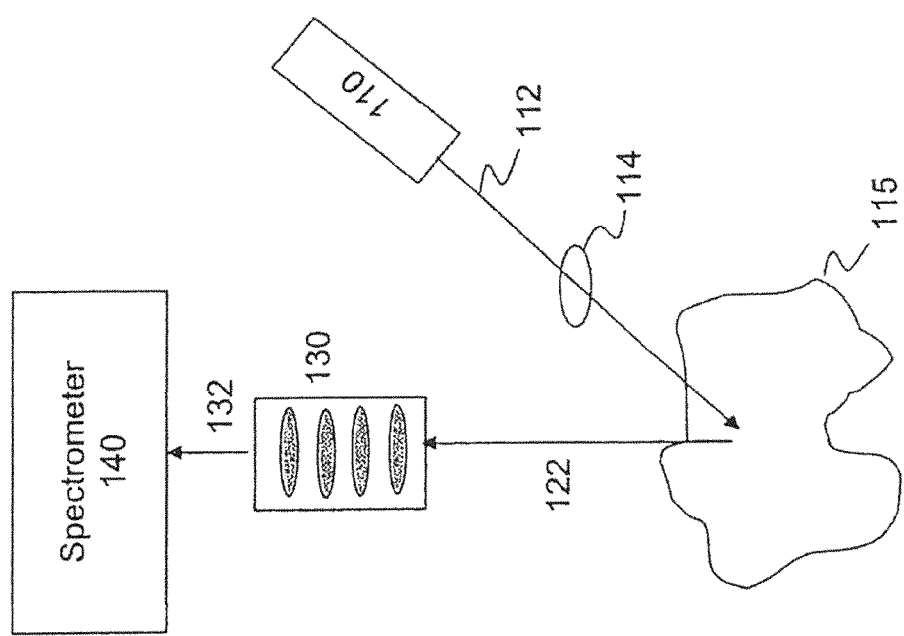
FIG. 1 is a spectroscopy system according to one embodiment of the disclosure.

FIG. 1 is a spectroscopy system according to one embodiment of the disclosure. The system shown in FIG. 1 can be configured as a handheld device, point detection device, or a standoff detector device. The spectroscopy device of FIG. 1 can be used, for example, to simultaneously obtain spectroscopic images of a sample. The images can define different spectroscopic modes such as laser scattering, ultraviolet laser induced fluorescence (UV-LIF) and laser induced breakdown spectroscopy (LIBS). In FIG. 1, illumination source 110 provides a plurality of illuminating photons to sample 115. Optical device 114 may include one or more light gathering optics and it may optionally be used to focus, filter or direct illumination photons 112 to sample 115. Once illuminated, sample photons 122 can be collected by gathering optics 130 and directed to spectrometer 140. Spectrometer 140 can be configured to receive and process different types of spectra simultaneously. In one embodiment, spectrometer 140 receives and processes sample photons for simultaneously forming Raman and LIBS spectra for sample 115. In one embodiment, first sample photons are processed to obtain Raman spectra for the sample and then second sample photons are processed to obtain LIBS spectra for the sample.

The exemplary system of FIG. 1 can include a fiber array spectral translator ("FAST). For example, transmission line 132 can comprise a fiber bundle such that a first end of the fiber bundle optically communicates with gathering optics 130 while the second end of the fiber bundle communicates with spectrometer 140. The first end of the fiber bundle can comprise of a two dimensional non-linear array of fiber bundles. The second end of the fiber bundle can comprise of curvilinear array of fibers wherein curvilinear may include a straight line as well as a curved line configuration. In an alternative embodiment, the system of FIG. 1 may additionally include an optical filter such as Liquid Crystal Tunable Filter (LCTF), Monolithic Crystal Filter (MCF) or an Acousto-Optic Tunable Filter (AOTF). The system of FIG. 1 may also be configured for use with Computed Tomography Imaging Spectroscopy (CTIS).

Figure 2A:
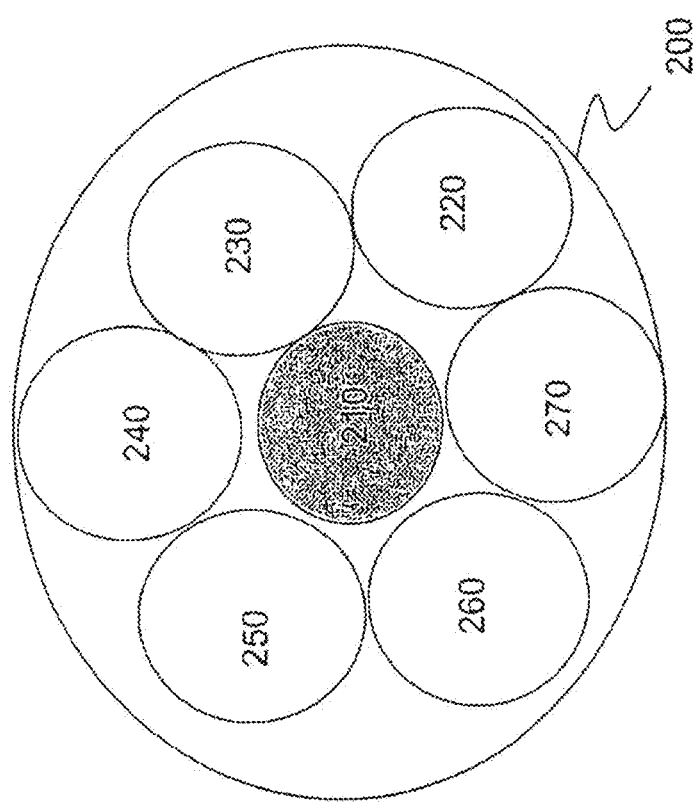
FIG. 2A is an exemplary structured illumination configuration according to one embodiment of the disclosure.

FIG. 2A is an exemplary structured illumination configuration according to one embodiment of the disclosure. In FIG. 2A, illumination circle 200 represents an illuminated area of a sample. Area 200 can be illuminated with photons having a first wavelength and region 210 can be illuminated with photons having a second wavelength. Thus, area 200 can be illuminated with photons of a first wavelength to obtain a Raman spectra for area 200. Thereafter, region 210 can be illuminated with photons of a second wavelength to obtain LIBS spectra for region 210. The sample can be illuminated to obtain Raman spectra before LIBS. Alternatively, the sample can be illuminated to obtain LIBS spectra before Raman. In still another embodiment, the annulus area between rings 200 and 210 can be used to obtain LIBS spectra and region 210 can be used for obtaining Raman spectra.

In an embodiment, area 200 and region 210 cane be illuminated simultaneously with photons of different wavelength. Photons of a first wavelength can illuminate the entire area 200 (or the annulus region between area 200 and region 210), and photons of a second wavelength can illuminate region 210. Raman spectra can be collected from regions 220-270, while LIBS spectra is simultaneously collected from region 210. In the even that the region 210 is illuminated simultaneously with photons of the first and second wavelength, optical filters and detectors can be used to remove unwanted sample photons.

In another embodiment of FIG. 2A, each of regions 220-270 shows a region of the sample from which Raman-scattered photons may be collected. Region 210 can represent a region for which LIBS can be implemented to obtain an atomic signature of the sample under study. The atomic signature of the sample can define the chemical identify of the sample at region 210. Regions 210-270 can have the shape of a circle, an ellipse, a rectangle, a square, a hexagon or any other shape. The combined analysis is advantageous in that it provides a significant synergistic performance of Raman and LIBS. That is, the structured illumination provides the specificity of Raman molecular spectroscopy along with LIBS elemental spectroscopy.

The structured illumination configuration of FIG. 2A can reflect an arrangement of the illumination sources (not shown). For example, the illumination configuration can comprise a first laser source for illuminating the entire region with photons of a first frequency and a second laser source for illuminating region 210 with photons of a second frequency. The arrangement of the first and second laser sources can be adapted to provide the structured illumination of FIGS. 2A-2C or variations thereof.

As stated, area 200 and region 210 can be illuminated simultaneously or sequentially. In one embodiment, area 200 is first illuminated with photons of the first wavelength. Sample photons can then be collected from each of the regions 220-270. Next, region 210 can be illuminated with photons of a second wavelength and sample photons can be collected therefrom. In an embodiment where the first wavelength provides a Raman spectrum and the second wavelength provides laser induced breakdown spectroscopy of the sample, collecting Raman photons from the sample before implementing laser induced breakdown spectroscopy enables Raman detection before a region of the sample (e.g., region 210) may be partially destroyed by LIES.

In another embodiment, area 200 is illuminated substantially simultaneously with region 210. That is, photons of the first wavelength and photons of the second wavelength are directed to the sample at substantially the same time to independently collect sample photons from area 200 and region 210. According to this embodiment, the detection and analysis of the sample can be implemented simultaneously. Such implementation can be particularly beneficial for large samples where a sample is divided into a number of segments and each segment is analyzed independently of the remaining segments.

Figure 2B:
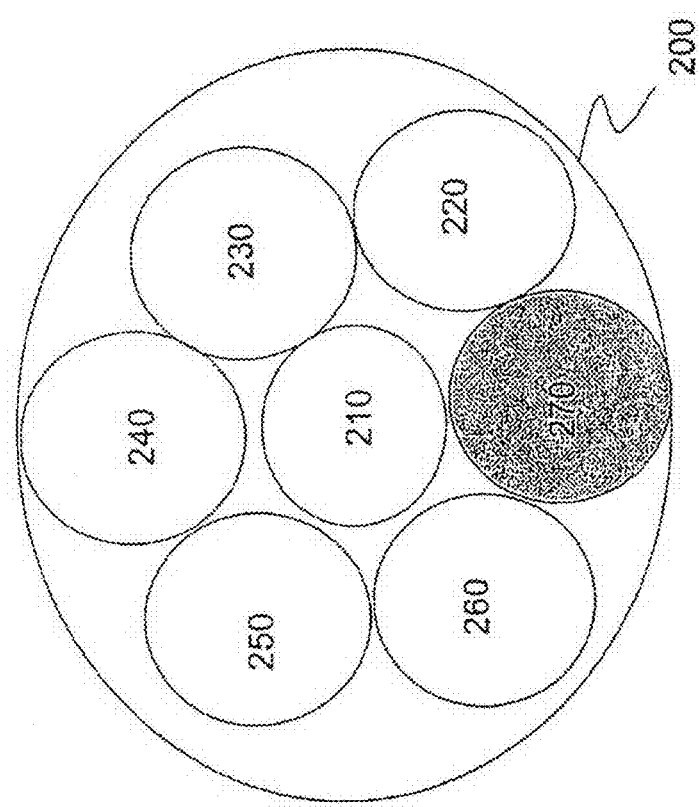
FIG. 2B is another exemplary structured illumination configuration according to one embodiment of the disclosure.

FIG. 2B is another exemplary structured illumination configuration according to an embodiment of the disclosure. In the structured illumination configuration of FIG. 2B, the area 200 is illuminated with photons of a first wavelength and region 270 can be illuminated with photons of a second wavelength. The photons of the first wavelength can elicit Raman spectra for regions 210-260 while sample photons collected from region 270 can identify the sample through LIES. The illumination of area 200 and region 270 can overlap. That is, both area 200 and region 270 can be illuminated simultaneously.

Figure 2C:
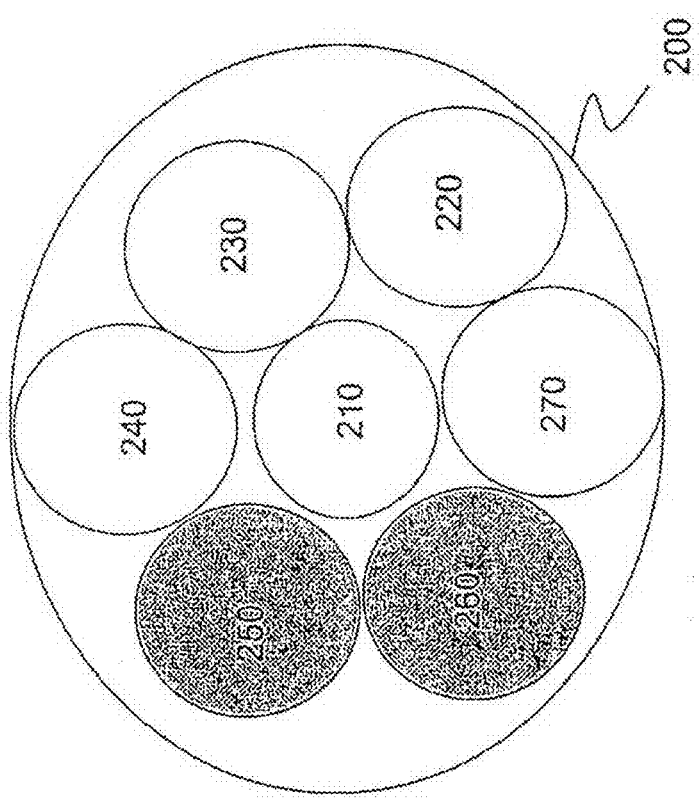
FIG. 2C is yet another exemplary structured illumination configuration according to one embodiment of the disclosure.

Similarly, FIG. 2C is yet another exemplary structured illumination configuration according to one embodiment of the disclosure. In FIG. 2C, area 200 is illuminated with photons having a first wavelength to collect sample photons from regions 210, 220, 230, 240 and 270. Photons having a second wavelength illuminate different regions of the sample to provide sample photons from regions 250 and 260. The sample photons from different regions 210-270 can be used to identify the sample. For example, if Raman spectra is collected from regions 210, 220, 230, 240 and 270 and regions 250 and 260 are used for LIES, the sample under study can be identified by its Raman spectra and its atomic emission.

FIG. 3 is a schematic representation for an apparatus according to one embodiment of the disclosure. FIG. 3 can provide illumination source as well as the collection optics and the spectroscopy device. More specifically, FIG. 3 provides integrated handheld device 300 for sample detection and analysis. Handheld device 300 can include illumination source 315 and collection point 316. The illumination source can be integrated with the handheld device or it can be provided as a nozzle attachment. In one embodiment of the disclosure, nozzle 316 can be configured to collect sample photons. Further, the illumination source can be configured to provide structured illumination for sample 320. In FIG. 3, sample 320 is illuminated with photons of a first wavelength at region 310 and photons of a second wavelength at region 330. Regions 310 and 330 can overlap as shown. Photons collected from region 310 can provide laser induced breakdown spectroscopy and photons collected from the remainder of region 330 can be used to construct a Raman spectra for the sample. Both regions 310 and 330 of sample 320 can be illuminated simultaneously by an illumination source configured to provide photons of a first wavelength to region 330 and photons of a second wavelength to region 310. The illumination source may comprise two laser illumination devices concentrically positioned to form an annulus and to provide the illumination shown in FIG. 3.

FIG. 4A shows LIBS spectra collected from a sample. Specifically, FIG. 4A shows the presence of Yersinia Rhodei (YR) 401, MS2 bacteriophage virus 402, and bacillus globigii 403 as indicated by each of their respective spectra. FIG. 4B shows Raman spectra collected from the sample of FIG. 4A. The Raman spectrum for each of YR 411, MS2 virus 412 and BG 413 are shown. In addition, at the bottom of FIGS. 4A and 4B, confusion matrices are shown for each of the Raman, LIES and combined Raman/LIBS sensing, respectively, of YR, MS2 and BG.

A confusion matrix quantifies the degree or relatedness of spectra within specific classes contained in a training dataset, as well as providing an estimate of the degree of specificity inherent in the analysis and dominant sources of interference between classes (crosstalk). In this example, the classes are comprised of Yr, MS2 and BG. The confusion matrix is calculated by organizing the species-level Raman spectra into three unique classes. PCA analysis was performed and the first 10 PCs were employed to construct a supervised Mahalanobis distance model boundary classifier for each of the 3 biological classes. The classifier consisted of a mean spectrum, covariance matrix, and an ellipsoidal boundary. Each spectrum, as a point in the N=10 dimensional PC dataspace, was compared with the ellipsoidal boundaries. The minimum distance classification mile (nearest neighbor approach) was used whereby a spectrum was deemed a member of a particular class (ellipsoidal boundary) if its distance from that class was less than its distance from all other classes. Each row in the confusion matrix is the biological identity of the spectra, and the column entries show how the Mahalanobis distance based classifier classified the spectra. A perfect classifier has entries only along the diagonal. Confusion matrices are a predictor of the specificity of an identification algorithm in which the diagonal elements are correlated with the probabilities of correct identification (Pd) for each of the species, while the off-diagonal elements correlate with the probability of false positive (PI). The confusion matrix can change depending on the spectral range and number of principal components employed to construct the MD model. In the confusion matrices of FIGS. 4A and 48, it is evident that there is a reduction in probability of false positive detections in the Raman/LIBS combined approach relative to Raman or LIBS operating alone.

Figure 5:
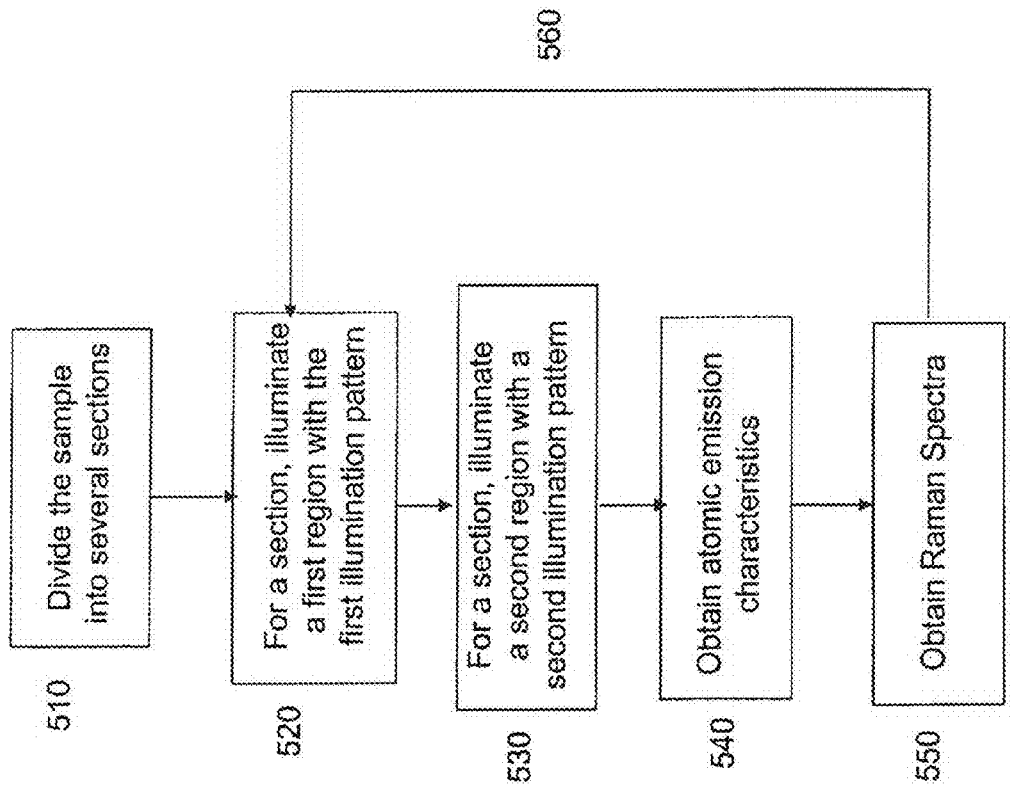
FIG. 5 is an exemplary algorithm according to an embodiment of the disclosure. Detailed Description.

FIG. 5 is an exemplary algorithm according to an embodiment of the disclosure. The exemplary algorithm of FIG. 5 can define a software or a fianware. The exemplary algorithm of FIG. 5 can be used with the system of FIG. 1 or apparatus of FIG. 3. In the optional step 510, the sample is visually divided into several sections. For example, the sample can be visually divided into a grid and each grid (section) can be analyzed independently. In step 520, a selected section of the sample is illuminated with photons of a first wavelength to obtain a first sample photons. The first sample photons can be used for Raman spectroscopy. In step 530, the selected section is illuminated with photons of a second wavelength to obtain second sample photons. The second sample photons can be used for laser induced breakdown spectroscopy. Steps 520 and 530 can be implemented substantially simultaneously or sequentially.

The first sample photons can be used to obtain the Raman spectra for the sample at step 540. The information can also be used to obtain a spatially accurate, wavelength resolved image of the section under study. That is, the spatially accurate, wavelength resolved image of the sample can be obtained for the Raman spectra as well as the LIBS spectra. A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest. The second sample photons can be used to obtain the atomic characteristic of the sample in step 550. The results from steps 540 and 550 can be used to section of the sample under study. Steps 520-550 can be repeated to study different visual sections of the sample as shown by arrow 560.

In another embodiment, the disclosure relates to a method and apparatus for detecting and identifying chemical or biological agents, including aerosols and low vapor pressure chemicals by using electrostatic collection devices with hyperspectral Raman imaging devices. The detection processes can be implemented without using reagents. An exemplary system can include: (1) an electrostatic collector for particulate collection and low vapor pressure chemical aerosol collection; (2) an autonomous surface deposition subsystem providing concentrated threat agents; (3) a hyperspectral Raman imaging sensor optionally having a low-power imaging sensor, a digital camera for sample focusing and an imaging spectrometer for generating spatially-resolved Raman spectra with sampling statistics necessary to differentiate target from background: and (4) a decision making algorithm for threat agent identification in the presence of clutter or background noise.

In another embodiment, the disclosure relates to a reagentless detector for biological threats in water. Biological sample variables include: genetic near neighbors, strain, serotype, growth conditions and viability. To identify the substance, Mahalanobis Distance correlation metric can be used. In a method according to one embodiment, detection and identification of waterborne threats without using reagents comprises the following process steps: sample collection; agent pre-concentration; detection and identification; automated decision making; and data management. The agent pre-concentration step can include: sample collection, water-contaminant pre-concentration, and sample deposition. The detection and identification step can include optical microscopy as well as Raman spectroscopy and imaging. The automated decision making step may include one or more algorithm for analyzing the spectroscopy results and identifying the sample.

Figure 6:
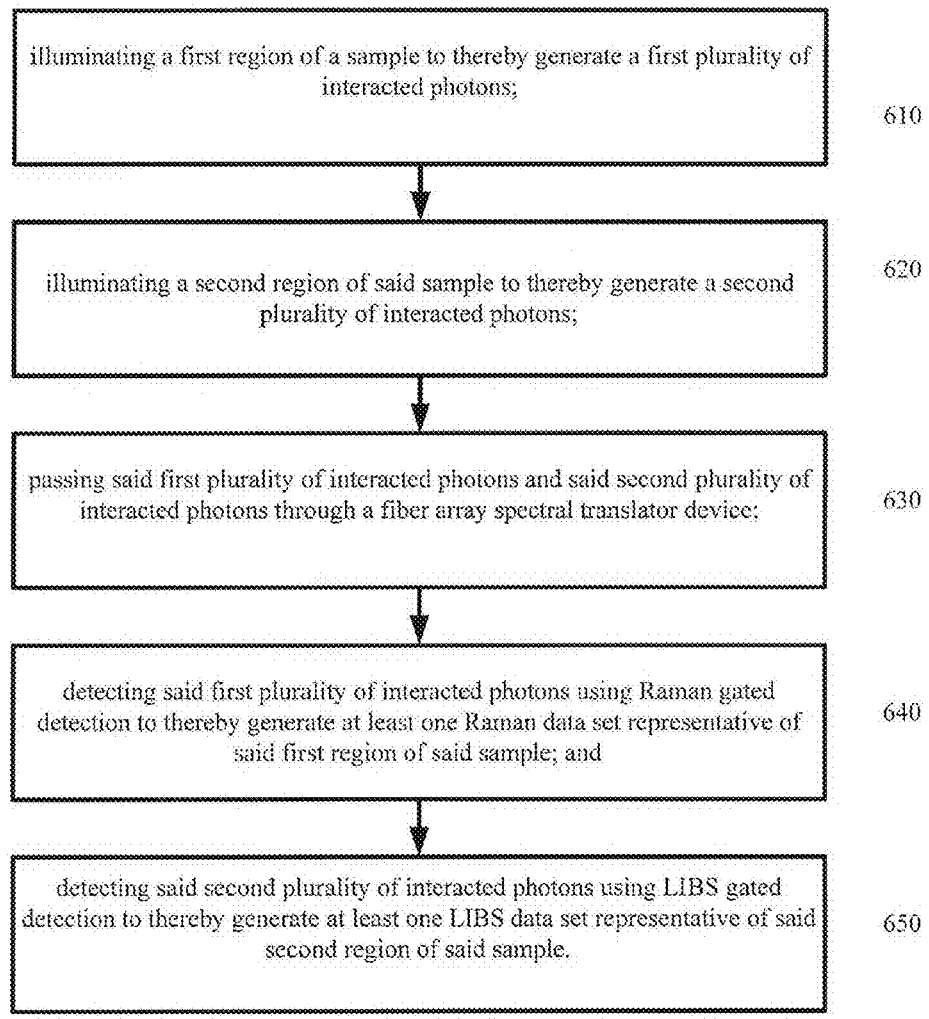
FIG. 6 is representative of a method of the present disclosure.

FIG. 6 is representative of a method of the present disclosure. The method 600 comprises illuminating a first region of a sample to thereby generate a first plurality of interacted photons in step 610. In step 620 a second region of said sample is illuminated to thereby generate a second plurality of interacted photons. In step 630 said first plurality of interacted photons and said second plurality of interacted photons are passed through a'fiber array spectral translator device. In step 640 said first plurality of interacted photons are detected using Raman gated detection tot thereby generate at least one Raman data set representative of said first region of said sample. In step 650 said second plurality of interacted photons are detecting using LIBS gated detection to thereby generate at least one LIBS data set representative of said second region of said sample.

In one embodiment, the present disclosure provides for a method wherein a first region of a sample and a second region of a sample are illuminated sequentially. In such an embodiment, the first region and the second region may be the same. In another embodiment, the first region and the second region may comprise two-dimensional non-overlapping regions. In yet another embodiment, the first region and the second region may comprise two-dimensional regions that partially overlap.

When operating in a sequential modality, the same fiber or fibers of the fiber array spectral translator device may be associated with said first region and said second region of the sample. In another embodiment, the fiber or fibers of the fiber array spectral translator device may be associated with different regions of the sample.

When operating in a sequential modality, a Raman grating array and a LIBS grating array may be incorporated into a single spectrometer. In one embodiment, use of Raman grating array and a LIBS grating array may configured to switch between Raman data acquisition and LIBS data acquisition. In one embodiment, fibers associated with a region of the sample under Raman analysis may be configured so as to effectively transmit photons scattered by that region to a Raman grating array. In another embodiment, fibers associated with a region of the sample under LIBS analysis may be configured so as to effectively transmit photons plasma emitted by that region to a LIBS grating array.

In one embodiment, the present disclosure provides for a method wherein a first region of a sample and a second region of a sample are illuminated simultaneously. In such an embodiment, said first region and said second region may be unique. This may mean that the first region and the second region comprise two-dimensional non-overlapping regions of the sample. In such an embodiment, a predetermined number of fibers of the fiber array spectral translator device are associated with a first region and a predetermine number of fibers is associated with a second region. In one embodiment, no fiber associated with the first region is also associated with the second region.

When operating in a simultaneous modality, fibers associated with a region of the sample under Raman analysis are configured so as to effectively transmit photons scattered by that region of the sample to a Raman spectrometer. This Raman spectrometer may comprise a Raman grating array. A Raman spectrometer may operate so as to effectively separate the plurality of scattered photons into a plurality of wavelength hands. A Raman detector may then detect these scattered photons and generate a Raman data set. Fibers associated with a region of the sample under LIBS analysis are configured so as to effectively transmit photons plasma emitted by that region of the sample to a LIBS spectrometer. This LIBS spectrometer may comprise a LIBS grating array. A LIBS spectrometer may operate so as to effectively separate a plurality of plasma emitted photons into a plurality of wavelength bands. A LIBS detector may then detect the plasma emitted photons and generate a LIBS data set.

The embodiments of the methods present disclosure may further comprise illuminating a first region and a second region of a sample using structured illumination. In one embodiment, a first region may be illuminated using a first wavelength and a second region may be illuminated using a second wavelength. A frequency doubling crystal may be used in one embodiment to enable excitation of regions of a sample with multiple excitation wavelengths and a single illumination source.

In one embodiment, structured illumination may further comprise illuminating a first region of a sample with a first illumination pattern and a second region of a sample with a second illumination pattern. In one embodiment, these first and second illumination patterns maybe the same. In another embodiment, these first and second illumination patterns may be different. Illumination patterns may be selected from the group consisting of, but not limited to: a square, a rectangle, a circle, a annulus, an ellipse, and combinations thereof.

In one embodiment, at least one of said first region of a sample and a second region of sample are illuminated using at least one of: continuations wave excitation, pulsed laser excitation, and combinations thereof.

In one embodiment, at least one of Raman data acquisition and LIBS data acquisition may comprise the use of time-gated detection. The combination of pulsed laser excitation and time-gated detection for the detection of threat agents is more fully described in U.S. patent application Ser. No. 12/802,994, filed on Jun. 17, 2010, entitled "Raman Chemical Imaging of Threat Agents Using Pulsed Laser Excitation and Time-Gated Detection," hereby incorporated by reference in its entirety.

In one embodiment, time-gated detection may comprise configuring a gating element (which may comprise an electronic signal) to acquire data at a certain time after illumination of the sample. In another embodiment, time-gated detection may comprise configuring a gating element to only acquire data for a certain predetermined period of time. In one embodiment, for Raman gated detection, this predetermined period of time may comprise a Raman emission time. In another embodiment, for LIBS gated detection this predetermined period of time may comprise a LIBS emission time.

In one embodiment, a method of the present disclosure may further comprising analyzing at least one of said Raman data set and said LIBS data set to thereby detect and/or identify an unknown sample. In one embodiment, this unknown sample may comprise an explosive material, a chemical material, a biological material, a hazardous material, a non-threat material and combinations thereof. In another embodiment, the unknown sample may comprise and explosive residue or a material associated with explosive materials, such as a binding element.

This analysis may further comprise comparing at least one of said Rman data set and said LIBS data set to a reference data base wherein said reference data base comprises at least one of a reference Raman data set associated with a known sample and a reference LIBS data set associated with a known sample. In one embodiment, this comparison may comprise applying one or more chemometric techniques. Such chemometric technique may be selected from the group consisting of: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion, and combinations thereof. In another embodiment, this analysis may comprise applying a fusion algorithm to said Rman data set and said LIES data set to thereby generate a fused data set. In one embodiment this fused data set may be compared to a reference fused data set. This may be achieved using a chemometric technique.

In one embodiment, this fusion may be accomplished using fusion software. This software may comprise ChemImage's FIST ("Forensic Integrated Search") technology, available from ChemImage Corporation, Pittsburgh, Pa. This technology is more fully described in pending U.S. patent application Ser. Nos. 11/450,138, filed on Jun. 9, 2006, entitled "Forensic Integrated Search Technology"; 12/017,445, filed on Jan. 22, 2008, entitled "Forensic Integrated Search Technology with Instrument Weight Factor Determination"; 12/196,921, filed on Aug. 22, 2008, entitled "Adaptive Method for Outlier Detection and Spectral Library Augmentation"; and 12/339,805, filed on Dec. 19, 2008, entitled "Detection of Pathogenic Microorganisms Using Fused Sensor Data". Each of these applications are hereby incorporated by reference in their entireties.

In another embodiment, image weighted bayesian fusion may be used. In another embodiment, the present disclosure provides for ChemFusion Improvements. Such improvements include the use of grid search methodology to establish improved weighting parameters for individual sensor modality classifiers under JFIST Bayesian architecture.

Figure 7:
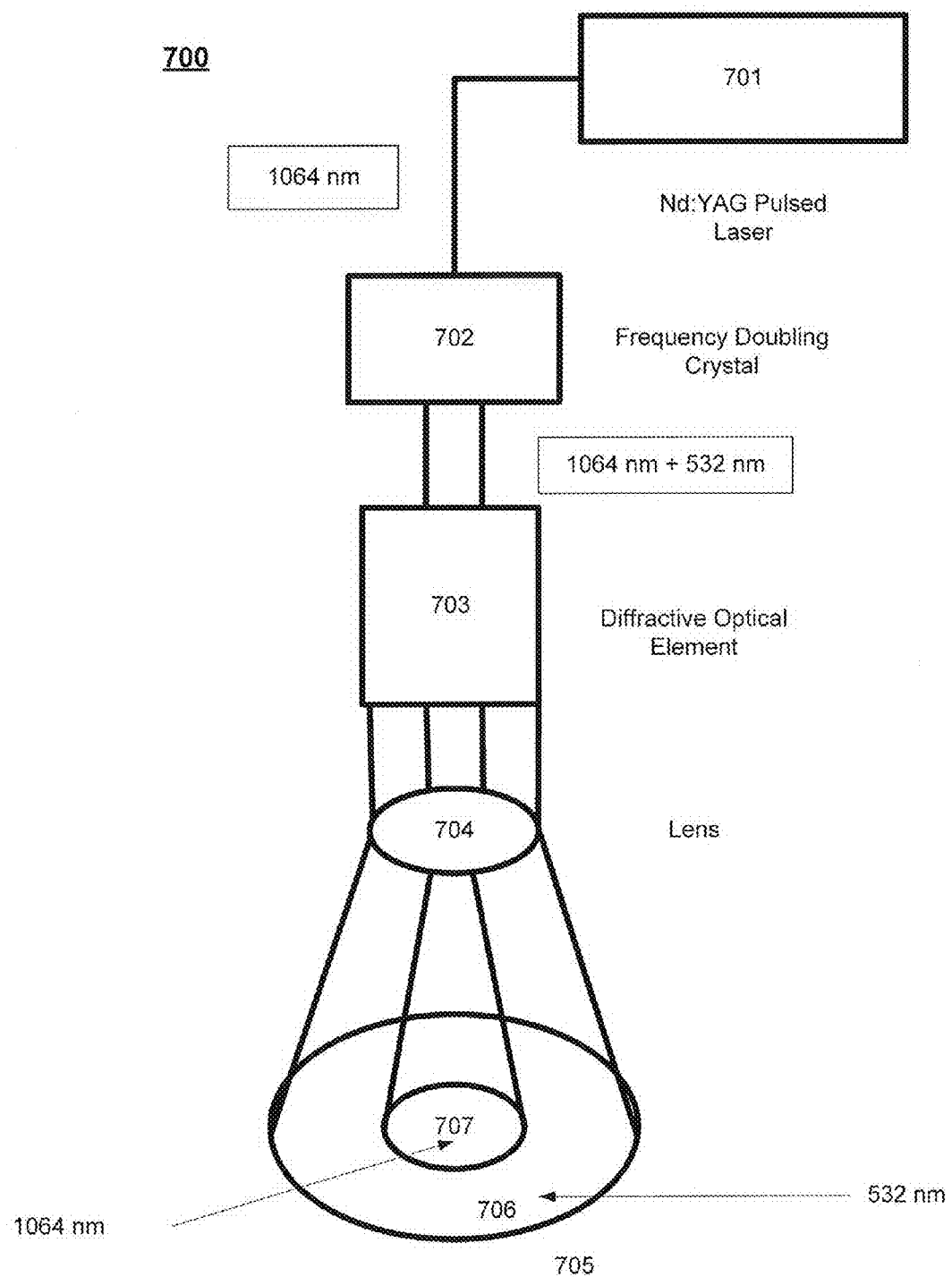
FIG. 7 is a schematic representation of a system of the present disclosure.

FIG. 7 is a schematic representation of a system of the present disclosure. The system 700 may comprise an illumination source, illustrated in FIG. 7 as a Nd:YAG pulsed laser 701. However the system 700 may be configured to operate with other illumination sources including those configured for continuous wave expiation, pulsed laser excitation, and combinations thereof. The illumination light of the illumination source 701 may pass through a frequency doubling crystal 702. The frequency doubling crystal 702 provides for the capability to illuminate a sample with multiple excitation wavelengths using a single illumination source. The illumination source 701 may illuminate at least one of a first region of a sample 706 and a second region of a sample 707. In FIG. 7, the entire sample is referred to as element 705. In FIG. 7, the first region of the sample 706 and the second region of the sample 707 are illustrated as non-overlapping regions. However, in another embodiment, the first region and the second region may be the sample or comprise partially overlapping regions. One or more lens elements 704 may be used to focus the light, collect scattered and plasma emitted photons, and combinations thereof. Diffractive optical element 703 may detect the scattered and/or plasma emitted photons and thereby generate Raman and or LIBS data sets representative of the respective regions of the sample under such interrogation.

Figure 8:
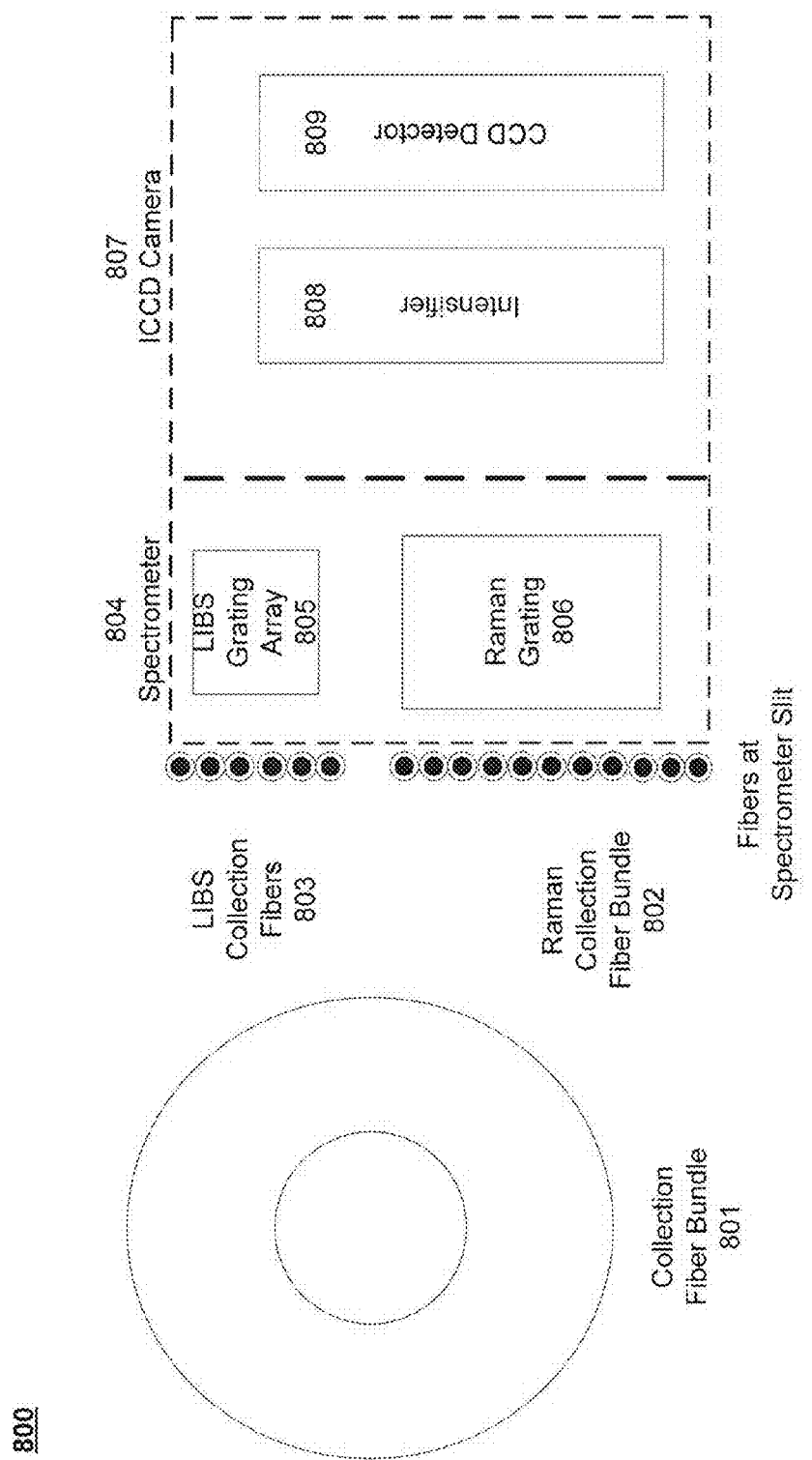
FIG. 8 is a detailed schematic representation of a system of the present disclosure.

FIG. 8 illustrates a possible detailed configuration of the system of FIG. 7. In one embodiment, the Diffractive Optical Element 703 may comprise a spectrometer 804 and/or detector 807. In FIG. 8, the detector 807 is illustrated as comprising a ICCD camera (comprising an intensifier 805 and a CCD detector 809), however other embodiments contemplated by this disclosure may provide for the use of other detectors known in the art.

Referring again to the spectrometer 804 of FIG. 8, in one embodiment, a LIBS grating array 805 and a Raman grating array 806, may be incorporated into a single spectrometer 804. As can be seen from FIG. 8, collection fibers associated with a region of a sample under LIBS analysis 803 may be operatively coupled to a LIBS grating array 805. Similarly, collection fibers associated with a region of a sample under Raman analysis 802 may be operatively coupled to a Raman grating array 806.

Figure 9B:
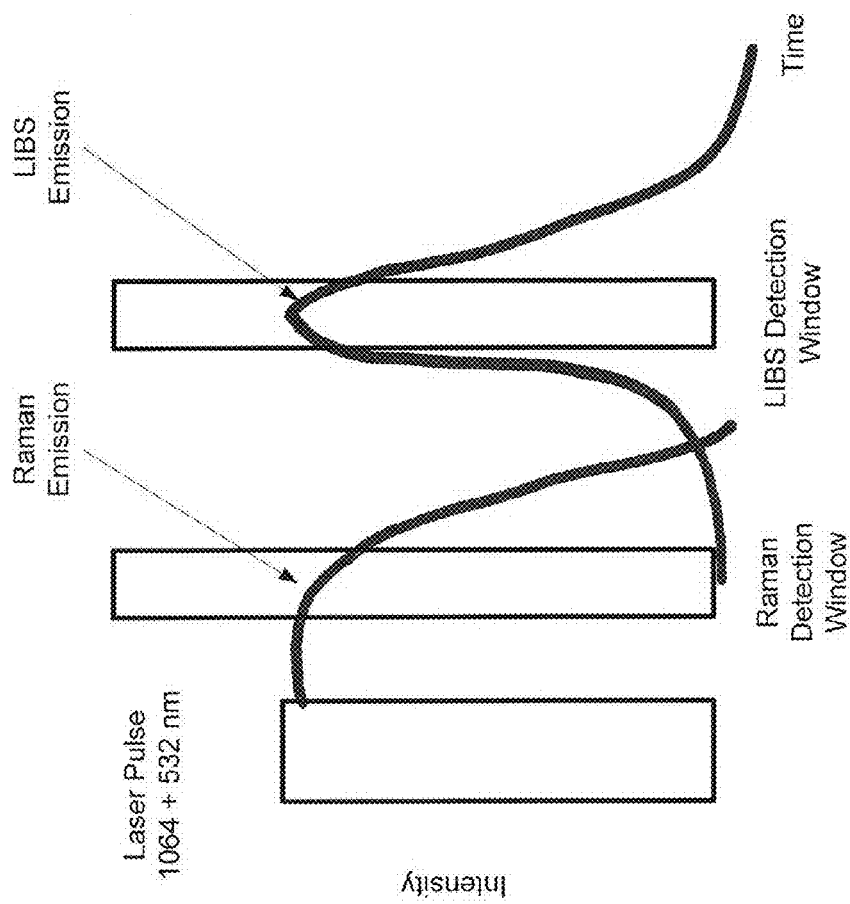
FIG. 9B is a schematic representation of time-gated detection capabilities of the system and method of the present disclosure.
Figure 9A:
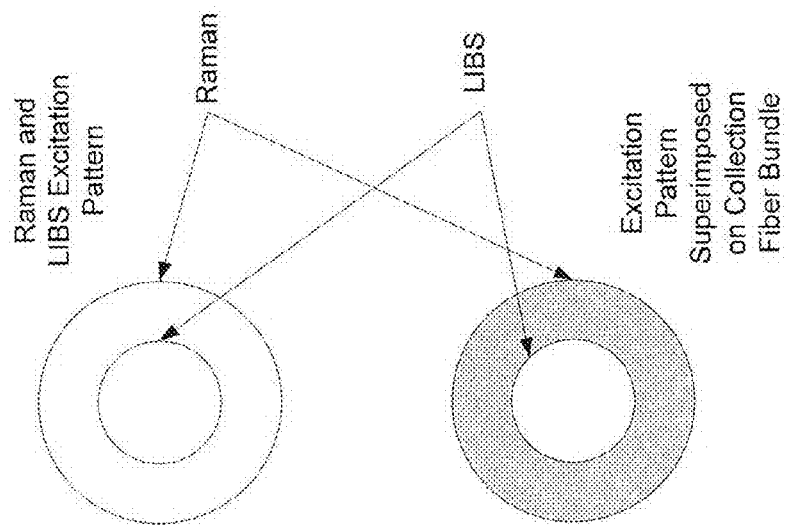
FIG. 9A is a schematic representation of a structured illumination pattern that may be used in conjunction with the system and method of the present disclosure.

FIG. 9A is provided to illustrate one embodiment of an illumination pattern that may be utilized in conjunction with the system and method of the present disclosure. However, this illumination pattern is provided only as an example and in no way limits the illumination patterns that may be used herein. FIG. 9B is a schematic representation of time-gated detection of Raman and LIBS detection. FIG. 9B is illustrative of the different emission times of both Raman and LIBS.

Figure 10:
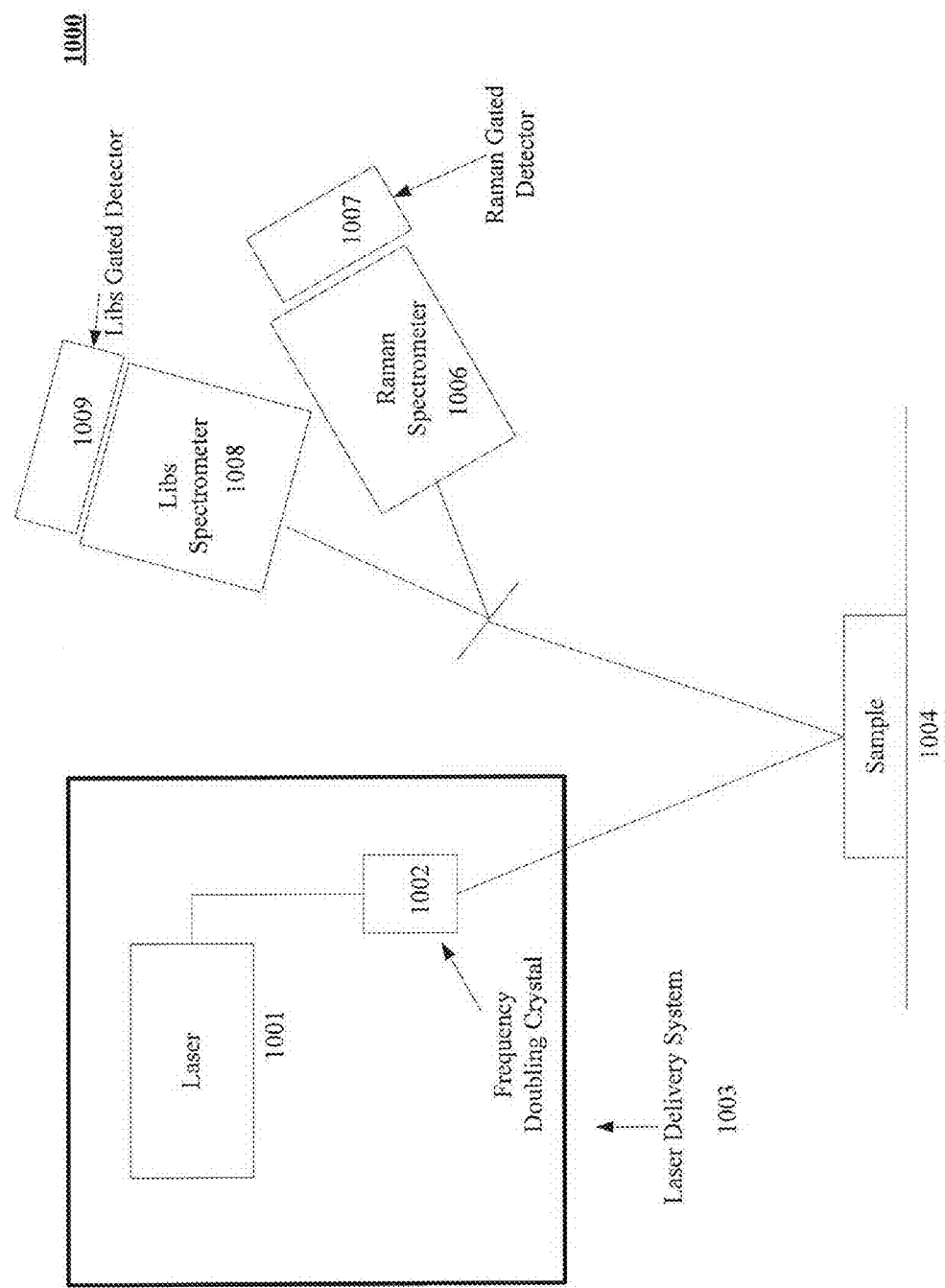
FIG. 10 is a schematic representation of a system of the present disclosure.

FIG. 10 is a schematic representation of a system of the present disclosure. The system 1000 may comprise an illumination source, illustrated in FIG. 10 as a laser light source 1001, to illuminate a sample 1004 with a plurality of illuminating photons. These photons may pass through a frequency doubling crystal 1002. In one embodiment, the illumination source 1001 and the frequency doubling crystal 1002 may be referred to collectively as a laser delivery system 1003.

Photons scattered by said sample 1004 may be directed to a Raman spectrometer 1006 by a directing element 1005. The Raman spectrometer 1006 may effectively separate a plurality of photons scattered by the sample 1004 into a plurality of wavelength bands. A Raman detector 1007 may be configured to detect these scattered photons and generate a Raman data set representative of the associated region of the sample 1004. This directing element 1005 may comprise a beam splitter, a mirror, a lens, or other device configured so as to effectively transmit different photons to different detectors. The directing element 1005 may also direct photons plasma emitted by the sample 1004 to a LIBS spectrometer 1008. The LIBS spectrometer 1008 may effectively separate a plurality of photons plasma emitted by the sample 1004 into a plurality of wavelength bands. A LIBS detector 1009 may be configured to detect these plasma emitted photons and generate a LIBS data set representative of the associated region of the sample 1004.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

What is claimed is:

1. A system comprising: an illumination source, wherein said illumination source is configured to illuminate at least one of: a first region of a sample to thereby generate a first plurality of interacted photons and a second region of said sample to thereby generate a second plurality of interacted photons; a fiber array spectral translator device, wherein said device comprises a two-dimensional array of optical fibers drawn in into a one-dimensional fiber stack so as to effectively convert a two-dimensional field of view into a curvilinear field of view and, a Raman spectrometer wherein said Raman spectrometer is configured so as to effectively separate said first plurality of interacted photons into a first plurality of wavelength bands; a LIBS spectrometer wherein said LIBS spectrometer is configured so as to effectively separate said second plurality of interacted photons into a second plurality of wavelength bands; a Raman detector to thereby generate a Raman data set representative of said first region; and a LIBS detector to thereby generate a LIBS data set representative of said second region of said sample.

2. The system of claim 1 wherein said first region and said second region comprise non-overlapping regions of said sample.

3. The system of claim 1 wherein at least one fiber of said fiber array spectral translator device is associated with said first region and wherein at least one fiber of said fiber array spectral translator device is associated with said second region.

4. The system of claim 3 wherein said fiber associated with said first region is configured so as to transmit said first plurality of interacted photons to said Raman spectrometer.

5. The system of claim 3 wherein said fiber associated with said second region is configured so as to transmit said second plurality of interacted photons to said LIBS spectrometer.

6. The system of claim 1 wherein said illumination source is configured so as to illuminate said first region and said second region simultaneously.

7. The system of claim 1 wherein said illumination source is configured for structured illumination.

8. The system of claim 1 wherein said illumination source is configured so as to illuminate said first region with a first excitation wavelength and said second region with a second excitation wavelength.

9. The system of claim 1 further comprising a frequency doubling crystal to achieve multi-wavelength illumination using one illumination source.

10. The system of claim 1 further comprising a means for enabling at least one of Raman time-gated detection and LIBS time-gated detection.

11. A method comprising: illuminating a first region of a sample to thereby generate a first plurality of interacted photons; illuminating a second region of said sample to thereby generate a second plurality of interacted photons; passing said first plurality of interacted photons and said second plurality of interacted photons through a fiber array spectral translator device; detecting said first plurality of interacted photons using Raman gated detection to thereby generate at least one Raman data set representative of said first region of said sample; and detecting said second plurality of interacted photons using LIBS gated detection to thereby generate at least one LIBS data set representative of said second region of said sample.

12. The method of claim 11 further comprising: receiving said first plurality of interacted photons and said second plurality of interacted photons at a two-dimensional end of said fiber array spectral translator device, wherein said device comprises: a two-dimensional array of optical fibers drawn into a one-dimensional fiber stack so as to effectively convert a two-dimensional field of view into a curvilinear field of view, at least one of said fibers is associated with said first region of said sample, and at least one of said fibers is associated with said second region of said sample.

13. The method of claim 12 further comprising: delivering said first plurality of interacted photons to a Raman grating array via said fiber associated with said first region of said sample, and delivering said second plurality' of interacted photons to a LIBS grating array via said fiber associated with said second region of said sample.

14. The method of claim 13 wherein said Raman grating array and said LIBS grating array are incorporated into one spectrometer.

15. The method of claim 13 wherein said Raman grating array is incorporated into a Raman spectrometer and said LIES grating array are incorporated into a LIBS spectrometer.

16. The method of claim 11 wherein at least one of said first region and said second region are illuminated using least one of: continuous wave laser excitation, pulsed laser excitation, and combinations thereof.

17. The method of claim 11 wherein said first region of said sample is illuminated using a first wavelength and said second region of said sample is illuminated using a second wavelength.

18. The method of claim 11 wherein said Raman gated detection comprises configuring data acquisition to occur during a predetermined period of time.

19. The method of claim 11 wherein said predetermined period of time is equal to a Raman emission time.

20. The method of claim 11 wherein said LIES gated detection comprises configuring data acquisition to occur during a predetermined period of time.

21. The method of claim 20 wherein said predetermined period of time comprises a LIBS emission time.

22. The method of claim 11 wherein said illumination of said first region and said second region of performed sequentially.

23. The method of claim 11 wherein said detection of said first plurality of interacted photons and said second plurality of interacted photons is performed simultaneously.

24. The method of claim 11 further comprising analyzing at least one of said Raman data set and said LIBS data set to thereby identify said sample as comprising at least one of: an explosive threat material, a biological threat material, a chemical threat material, a non-threat material, a material associated with threat materials, and combinations thereof.

25. The method of claim 24 wherein said analysis comprises comparing at least one of said Raman data set and said LIBS data set with one or more reference data sets wherein each reference data set is associated with a known sample.

26. The method of claim 25 wherein said comparison comprises applying at least one chemometric technique to at least one of said Raman data set and said LIBS data set.

27. The method of claim 11 further comprising fusing said Raman data set and said LIBS data set to thereby generate a fused data set.

28. The method of claim 17 further comprising analyzing said fused data set to thereby identify said sample as comprising at least one of: an explosive threat material, a biological threat material, a chemical threat material, a non-threat material, a material associated with threat materials, and combinations thereof.

29. The method of claim 28 wherein said analyzing comprises comparing said fused data set with a reference data set wherein said reference data set corresponds to a known sample.

30. The method of claim 29 wherein said comparison is achieved using at least one chemometric technique.

31. The method of claim 11 further comprising switching between acquisition of said Raman data set and acquisition of said LIBS dataset.

* * * * *